United States Patent
Lee et al.

(10) Patent No.: US 12,333,648 B2
(45) Date of Patent: Jun. 17, 2025

(54) METHOD AND APPARATUS FOR RECONSTRUCTING IMAGES OF INSIDE OF BODY OBTAINED THROUGH ENDOSCOPE DEVICE

(71) Applicant: MedInTech Inc., Seoul (KR)

(72) Inventors: Chiwon Lee, Namyangju (KR); Myungjoon Kim, Gwacheon (KR); Taehyeon Kim, Seoul (KR)

(73) Assignee: MedInTech Inc., Seoul (KR)

( * ) Notice: Subject to any disclaimer, the term of this patent is extended or adjusted under 35 U.S.C. 154(b) by 0 days.

(21) Appl. No.: 18/953,514

(22) Filed: Nov. 20, 2024

(65) Prior Publication Data

US 2025/0166298 A1    May 22, 2025

(30) Foreign Application Priority Data

Nov. 21, 2023    (KR) ............ 10-2023-0161846

(51) Int. Cl.
  *G06T 17/00*    (2006.01)
  *G16H 30/00*    (2018.01)
(52) U.S. Cl.
  CPC ............. *G06T 17/00* (2013.01); *G16H 30/00* (2018.01); *G06T 2210/41* (2013.01)
(58) Field of Classification Search
  CPC ..... G06T 17/00; G06T 2210/41; G06T 17/10; G06T 19/00; G06T 2207/10068; G06T 7/0012; A61B 34/20; A61B 90/361
  See application file for complete search history.

(56) References Cited

U.S. PATENT DOCUMENTS

| | | | |
|---|---|---|---|
| 2014/0051986 A1* | 2/2014 | Zhao | G06T 7/33 600/424 |
| 2017/0046833 A1* | 2/2017 | Lurie | G06T 17/20 |
| 2021/0015343 A1* | 1/2021 | Uyama | A61B 1/0005 |
| 2021/0256701 A1* | 8/2021 | Nozaki | G16H 50/30 |
| 2023/0136100 A1* | 5/2023 | Tata | A61B 1/000094 600/101 |
| 2023/0162380 A1* | 5/2023 | Soper | G06T 7/70 382/100 |

FOREIGN PATENT DOCUMENTS

| | | |
|---|---|---|
| KR | 10-1595297 B1 | 2/2016 |
| KR | 10-1595962 B1 | 2/2016 |
| KR | 10-2106694 B1 | 5/2020 |
| KR | 10-2022-0032195 A | 3/2022 |
| KR | 10-2022-0034458 A | 3/2022 |
| KR | 10-2553961 B1 | 7/2023 |

\* cited by examiner

*Primary Examiner* — Xilin Guo
(74) *Attorney, Agent, or Firm* — Harvest IP Law, LLP

(57) ABSTRACT

According to one embodiment of the present disclosure, there is disclosed a method of reconstructing images of the inside of the body that is performed by a computing device including at least one processor. The method includes: obtaining basic data including the pose information of an end of an endoscopic scope and a captured image of the inside of the body; and generating a three-dimensional (3D) final image of the inside of the body by reconstructing the basic data using feature points including the image information of the surface of the inside of the body for the basic data.

13 Claims, 6 Drawing Sheets

METHOD AND APPARATUS FOR RECONSTRUCTING IMAGES OF INSIDE OF BODY OBTAINED THROUGH ENDOSCOPE DEVICE

CROSS-REFERENCE TO RELATED APPLICATION

This application claims the benefit of Korean Patent Application No. 10-2023-0161846 filed on Nov. 21, 2023, which is hereby incorporated by reference herein in its entirety.

BACKGROUND

1. Technical Field

The present disclosure relates to technology for reconstructing images, and more particularly, to a method and apparatus for reconstructing images of the inside of the body obtained through an endoscope device.

2. Description of the Related Art

Endoscopes collectively refer to medical devices that enable a scope to be inserted into the body and a user to observe an organ without surgery or autopsy. Endoscopes enable a scope to be inserted into the body, light to be radiated, and the light reflected from the surface of the inner wall of the body to be visualized. Endoscopes are classified according to their purpose and target body part, and may be basically classified into rigid endoscopes, in which an endoscopic tube is made of metal, and flexible endoscopes, which are represented by digestive endoscopes.

Meanwhile, in the medical field, a technology for reconstructing organs in three dimensions (3D) using two-dimensional (2D) images is being actively applied. The same is true for endoscopic images. In the case of endoscopy, body regions to be captured have complex and irregular shapes in 3D, and thus, specific information can be obtained from three-dimensional (3D) images compared to 2D images, so that there is an advantage in 3D reconstruction. The technology for reconstructing 3D images using 2D images has developed from a traditional non-learning-based method that aligns images taken from multiple viewpoints and calculates parallax to a technology that uses a deep neural network based on depth information.

In the case of gastrointestinal endoscopy, the shapes of organs to be captured are complex and vary significantly from patient to patient, so that the movement of a scope for capturing images is also bound to be considerably irregular. In particular, in the case of large-intestinal endoscopy, the shapes of narrow and long tubes are captured, so that even when the movement of a scope is small, a change in the captured image is significant, and thus, it is difficult to obtain high-quality images for 3D reconstruction. Furthermore, for reconstruction, each area of the organ needs to have a characteristic shape. Due to the nature of endoscopic images, only information about the surface of the organ can be obtained. Furthermore, in the case of the stomach or large intestine, the surface colors are similar, so that it is difficult to perform reconstruction with high accuracy.

SUMMARY

The present disclosure is intended to overcome the problems of the above-described related art, and is directed to a method and device for reconstructing images of the inside of the body obtained through an endoscopic device that three-dimensionally reconstructs a captured organ based on an image obtained through an endoscope and information about an endoscopic scope.

However, objects to be achieved by the present disclosure are not limited to the object described above, and another object may be present.

According to one embodiment of the present disclosure for achieving the above-described object, there is disclosed a method of reconstructing images of the inside of the body that is performed by a computing device including at least one processor. The method includes: obtaining basic data including the pose information of an end of an endoscopic scope and a captured image of the inside of the body; and generating a three-dimensional (3D) final image of the inside of the body by reconstructing the basic data using feature points including the image information of the surface of the inside of the body for the basic data.

Alternatively, the feature points may be generated by a feature point generation model that is trained to represent patterns or textures formed on the surface of the inside of the body.

Alternatively, the patterns or textures may include at least one of blood vessels, irregularities, wrinkles, and lesions.

Alternatively, the feature point generation model may generate the feature points by representing the shape in which a drug is applied to the surface of the inside of the body.

Alternatively, the basic data may further include depth information from an end of the endoscopic scope to the surface of the inside of the body.

Alternatively, generating the 3D final image may include: generating point cloud data using the basic data and the feature points; and generating the final image reconstructing the point cloud data.

Alternatively, generating the 3D final image may include: generating modified point cloud data by removing points, present in a region out of a preset reference range, from the point cloud data; and generating the final image by reconstructing the modified point cloud data.

Alternatively, the method may further include determining the portion of the final image, in which the surface is smoothly reconstructed, to be a blind spot region, and the blind spot region may include the portion of the inside of the body that is not captured through the endoscopic scope.

According to one embodiment of the present disclosure for achieving the above-described object, there is disclosed a method of reconstructing images of an inside of a body that is performed by a computing device including at least one processor. The method includes: obtaining depth information from the end of an endoscopic scope to the surface of the inside of the body based on a captured image of the inside of the body by using a trained depth estimation model; obtaining the pose information of the end of the endoscopic scope based on the captured image by using a trained pose estimation model; and generating a three-dimensional (3D) final image of the inside of the body by using the depth information and the pose information.

Alternatively, the depth estimation model may be trained with first training data including a first training image of the inside of the body and a depth image corresponding to the first training image.

Alternatively, the pose estimation model may be trained with second training data including a second training image including feature points for the surface information of the inside of the body and pose information corresponding to the second training image.

Alternatively, obtaining the pose information of the end of the endoscopic scope by using the trained pose estimation model may include: generating a modified captured image by using feature points, generated using the feature point generation model trained to represent patterns or textures formed on the surface of the inside of the body, and the captured image; and obtaining the pose information of the end of the endoscope scope based on the modified captured image by using the trained pose estimation model.

Alternatively, the feature point generation model may generate the feature points by representing the shape in which a drug is applied to the surface of the inside of the body.

According to one embodiment of the present disclosure for achieving the above-described object, there is disclosed a computing device for reconstructing images of the inside of the body. The computing device includes: memory configured to store basic data including the pose information of the end of an endoscopic scope and a captured image of the inside of the body; and a processor configured to generate a three-dimensional (3D) final image of the inside of the body by reconstructing the basic data using the basic data and feature points including the image information of the surface of the inside of the body for the basic data.

According to one embodiment of the present disclosure for achieving the above-described object, there is disclosed a computing device for reconstructing images of the inside of the body, the computing device including: memory configured to store a captured image of the inside of the body; and a processor configured to obtain depth information from an end of an endoscopic scope to the surface of the inside of the body based on the captured image by using a trained depth estimation model, obtain the pose information of the end of the endoscopic scope based on the captured image by using a trained pose estimation model, and generate a three-dimensional (3D) final image of the inside of the body by using the depth information and the pose information.

According to one embodiment of the present disclosure, reconstruction is performed using feature points reflecting therein the surface information of the inside of the body with the characteristics of a body region taken into consideration, so that the accuracy of reconstruction can be improved.

In addition, according to one embodiment of the present disclosure, a blind spot region that is not captured by an endoscope may be identified based on surface information in a reconstructed image, so that the accuracy of an endoscopic procedure can be improved and convenience can be provided to a medical professional who needs to determine a blind spot region on his or her own.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Figure 1:
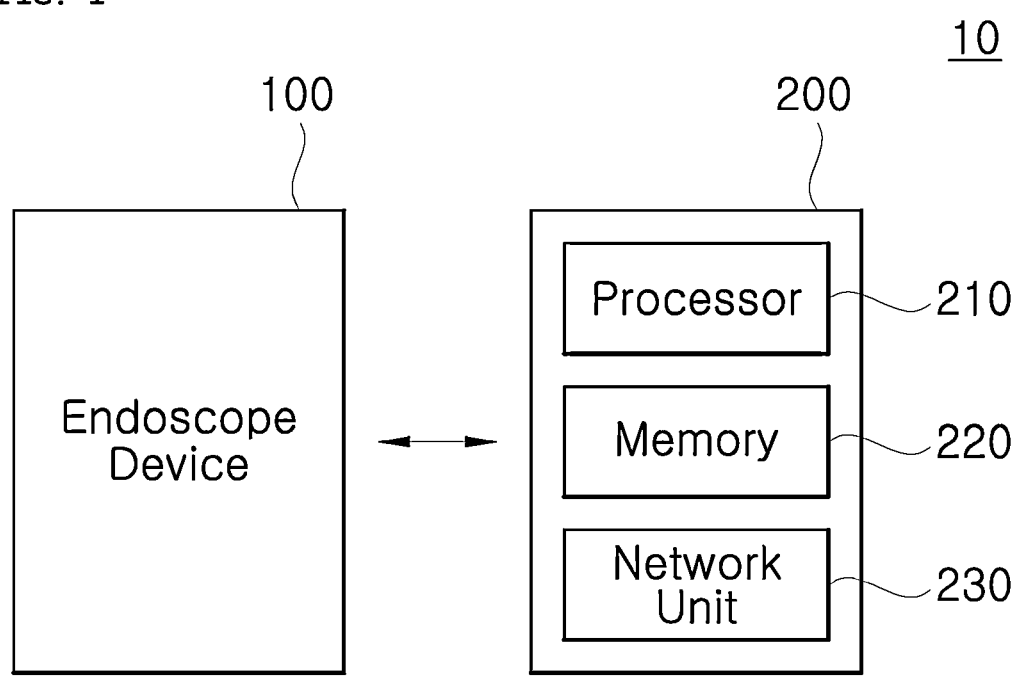
FIG. 1 is a block diagram of an endoscope system including an endoscope device and a computing device according to one embodiment of the present disclosure.

Embodiments of the present disclosure will be described in detail below with reference to the accompanying drawings so that those having ordinary skill in the art of the present disclosure (hereinafter referred to as those skilled in the art) can easily implement the present disclosure. The embodiments presented in the present disclosure are provided to enable those skilled in the art to use or practice the content of the present disclosure. Accordingly, various modifications to embodiments of the present disclosure will be apparent to those skilled in the art. That is, the present disclosure may be implemented in various different forms and is not limited to the following embodiments.

The same or similar reference numerals denote the same or similar components throughout the specification of the present disclosure. Additionally, in order to clearly describe the present disclosure, reference numerals for parts that are not related to the description of the present disclosure may be omitted in the drawings.

The term "or" used herein is intended not to mean an exclusive "or" but to mean an inclusive "or." That is, unless otherwise specified herein or the meaning is not clear from the context, the clause "X uses A or B" should be understood to mean one of the natural inclusive substitutions. For example, unless otherwise specified herein or the meaning is not clear from the context, the clause "X uses A or B" may be interpreted as any one of a case where X uses A, a case where X uses B, and a case where X uses both A and B.

The term "and/or" used herein should be understood to refer to and include all possible combinations of one or more of listed related concepts.

The terms "include" and/or "including" used herein should be understood to mean that specific features and/or components are present. However, the terms "include" and/or "including" should be understood as not excluding the presence or addition of one or more other features, one or more other components, and/or combinations thereof.

Unless otherwise specified herein or unless the context clearly indicates a singular form, a singular form should generally be construed to include "one or more."

The term "N-th (N is a natural number)" used herein can be understood as an expression used to distinguish the components of the present disclosure according to a predetermined criterion such as a functional perspective, a structural perspective, or the convenience of description. For example, in the present disclosure, components performing different functional roles may be distinguished as a first component or a second component. However, components that are substantially the same within the technical spirit of the present disclosure but should be distinguished for the convenience of description may also be distinguished as a first component or a second component.

Meanwhile, the term "module" or "unit" used herein may be understood as a term referring to an independent functional unit that processes computing resources, such as a computer-related entity, firmware, software or part thereof, hardware or part thereof, or a combination of software and hardware. In this case, the "module" or "unit" may be a unit composed of a single component, or may be a unit expressed as a combination or set of multiple components. For example, in the narrow sense, the term "module" or "unit" may refer to a hardware component or set of components of a computing device, an application program performing a specific function of software, a procedure implemented through the execution of software, a set of instructions for the execution of a program, or the like. Additionally, in the broad sense, the term "module" or "unit" may refer to a computing device itself constituting part of a system, an application running on the computing device, or the like. However, the above-described concepts are only examples, and the concept of "module" or "unit" may be defined in various manners within a range understandable to those skilled in the art based on the content of the present disclosure.

The term "model" used herein may be understood as a system implemented using mathematical concepts and language to solve a specific problem, a set of software units intended to solve a specific problem, or an abstract model for a process intended to solve a specific problem. For example, a neural network "model" may refer to an overall system implemented as a neural network that is provided with problem-solving capabilities through training. In this case, the neural network may be provided with problem-solving capabilities by optimizing parameters connecting nodes or neurons through training. The neural network "model" may include a single neural network, or a neural network set in which multiple neural networks are combined together.

The term "image" used herein may refer to multidimensional data composed of discrete image elements. In other words, the "image" may be understood as a term referring to a digital representation of an object that can be seen by the human eye. For example, the term "image" may refer to multidimensional data composed of elements corresponding to pixels in a two-dimensional image. The term "image" may refer to multidimensional data composed of elements corresponding to voxels in a three-dimensional image.

The foregoing descriptions of the terms are intended to help to understand the present disclosure. Accordingly, it should be noted that unless the above-described terms are explicitly described as limiting the content of the present disclosure, the terms in the content of the present disclosure are not used in the sense of limiting the technical spirit of the present disclosure.

FIG. 1 is a block diagram of an endoscope system 10 including an endoscope device and a computing device according to one embodiment of the present disclosure.

Referring to FIG. 1, the endoscope system 10 includes an endoscope device 100 configured to obtain various types of information including a medical image of the inside of the body, and a computing device 200 configured to reconstruct a medical image of the inside of the body in three dimensions by receiving and analyzing information about the inside of the body from the endoscope device 100.

The endoscope device 100 according to one embodiment of the present disclosure may be a flexible endoscope, or more specifically, a digestive endoscope. The endoscope device 100 may include a configuration capable of obtaining a medical image adapted to photograph the inside of a digestive organ and a configuration capable of, when necessary, allowing a tool to be inserted and a user to perform treatment or manipulation while viewing a medical image. The endoscope device 100 may include a control unit configured to control the overall operation of the endoscope device 100, a scope configured to be inserted into the body, and a drive unit configured to provide power required for the movement of the scope.

At least a part of the scope may be inserted into the body, and various cables, tubes, and surgical instruments may be inserted into the body through the scope, and medical imaging and procedures may be performed at the end of the scope. Meanwhile, a pose sensor or a depth sensor may be provided at the end of the scope. The pose sensor may obtain the 6-dimensional pose information of the scope and transmit it to the control unit of the endoscope device 100. The depth sensor may obtain depth information from the end of the scope to the surface of the inside of the body and transmit it to the control unit of the endoscope device 100. The pose or depth sensor may be detachable depending on the situation. For example, the pose or depth sensor may be installed when the scope is inserted into a model body, and may be detached when the scope is inserted into a real body.

The endoscope device 100 may obtain basic data including a medical image, i.e., a captured image, and may provide it to the computing device 200. The basic data includes a captured image of the inside of the body, and may include the pose information of the end of the endoscopic scope or depth information from the end of the endoscopic scope to the surface of the inside of the body.

The basic data may be obtained from the endoscope device 100. In this case, the endoscope device 100 may be an endoscope device 100 configured to be inserted into a real patient or a body model (a dummy, a mannequin, or the like) or an endoscope device 100 implemented in a virtual environment. The scope of the endoscope device 100 may be inserted into a real body or a model body. Alternatively, the basic data for a virtual body may be obtained by simulating the operation of the endoscope device 100 in a virtual space.

The computing device 200 of the present disclosure may reconstruct a 3D final image using the basic data received from the endoscope device 100. The final image may correspond to the inside of the body captured by the endoscope device 100.

The computing device 200 according to the one embodiment of the present disclosure may be a hardware device or part of a hardware device that performs the comprehensive processing and computation of data, or may be a software-based computing environment that is connected to a communication network. For example, the computing device 200 may be a server that performs an intensive data processing function and shares resources, or may be a client that shares resources through interaction with a server. Furthermore, the computing device 200 may be a cloud system in which a plurality of servers and clients interact with each other and comprehensively process data. Since the above descriptions are only examples related to the type of computing device 200, the type of computing device 200 may be configured in various manners within a range understandable to those skilled in the art based on the content of the present disclosure. Since the foregoing description is only one example related to the type of computing device 200, the type of computing device 200 may be configured in various manners within a range understandable to those skilled in the art based on the content of the present disclosure.

Referring to FIG. 1, the computing device 200 according to the one embodiment of the present disclosure may include a processor 210, memory 220, and a network unit 230. However, FIG. 1 illustrates only an example, and the computing device 200 may include other components for implementing a computing environment. Furthermore, only some of the components disclosed above may be included in the computing device 200.

The processor 210 according to an embodiment of the present disclosure may be understood as a constituent unit including hardware and/or software for performing computing operation. For example, the processor 210 may read a computer program and perform data processing for machine learning. The processor 210 may process computational processes such as the processing of input data for machine learning, the extraction of features for machine learning, and the calculation of errors based on backpropagation. The processor 210 for performing such data processing may include a central processing unit (CPU), a general purpose graphics processing unit (GPGPU), a tensor processing unit (TPU), an application specific integrated circuit (ASIC), or a field programmable gate array (FPGA). Since the types of processor 210 described above are only examples, the type of processor 210 may be configured in various manners within a range understandable to those skilled in the art based on the content of the present disclosure.

The processor 210 may reconstruct an organ captured by the endoscope device 100 in 3D by using information acquired through the endoscope device 100. In this case, the processor 210 may perform 3D reconstruction using the trajectory information of the end of the endoscopic scope that obtains the captured image, or may infer the pose information of the end of the endoscopic scope and depth information about the inside of the body from the captured image through an artificial neural network model and perform 3D reconstruction using the results of the inference.

More specifically, the processor 210 may generate point information acquired through the cloud data based on endoscope. A point cloud refers to a set of data points belonging to a 3D space, and individual points are gathered and represent a 3D shape or object.

The processor 210 may reconstruct a final image including a surface in 3D by using point cloud data, which is a set of points. The processor 210 may determine whether a portion that needs to be essentially captured during an endoscopic procedure is omitted by using the final image reconstructed in 3D. In the present specification, a portion that is omitted from capturing is referred to as a blind spot. The processor 210 may determine a blind spot region according to the reconstruction form of the final image. For example, the processor 210 may determine the portion of the final image where the surface is smoothly reconstructed to be a blind spot region, and the portion of the final image where the surface is roughly reconstructed to be a captured region.

Meanwhile, the basic data used by the processor 210 to generate the final image may vary depending on the data collection environment or reconstruction method.

For example, the basic data may include the captured image and the pose information of the end of the endoscopic scope, and may further include depth information from the end of the endoscopic scope to the surface of the inside of the body.

Meanwhile, in the process of reconstructing the 3D final image, the processor 210 may use the feature points included in the basic data, or may generate feature points based on basic data lacking feature points and then use the generated feature points. That is, the processor 210 may reconstruct the final image by using feature points that include image information about the surface information of the inside of the body in addition to the basic data. In the present disclosure, the feature points may refer to image elements representing the shape of the surface of the inside of the body. For example, they may refer to elements including fine shapes and colors observed on the surface of the inside of the body, such as wrinkles of an organ, and curves, irregularities, blood vessels, and lesions formed on the surface of an organ.

The processor 210 may train a feature point generation model to represent patterns or textures formed on the surface of the inside of the body, and may add feature points to the basic data by using the trained feature point generation model.

Alternatively, the processor 210 may train a feature point generation model to represent a shape in which a drug is applied to the body based on experimental images each taken after a drug is applied, and may add feature points to the basic data using the trained feature point generation model. The drug may be a staining agent that stains a specific region in an endoscopic procedure, and may be, for example, an indigo carmine solution. Meanwhile, a feature point generation method will be described in detail later.

The memory 220 according to an embodiment of the present disclosure may be understood as a constituent unit including hardware and/or software for storing and managing data that is processed in the computing device 200. That is, the memory 220 may store any type of data generated or determined by the processor 210 and any type of data received by the network unit 230. For example, the memory 220 may include at least one type of storage medium of a flash memory type, hard disk type, multimedia card micro type, and card type memory, random access memory (RAM), static random access memory (SRAM), read-only memory (ROM), electrically erasable programmable read-only memory (EEPROM), programmable read-only memory (PROM), magnetic memory, a magnetic disk, and an optical disk. Furthermore, the memory 220 may include a database system that controls and manages data in a predetermined system. Since the types of memory 220 described above are only examples, the type of memory 220 may be configured in various manners within a range understandable to those skilled in the art based on the content of the present disclosure. The memory 120 may be a non-transitory medium configured to store data and instructions in a tangible form, and is not a mere signal or transitory form.

The memory 220 may structure, organize, and manage data required for the processor 110 to perform computation, the combinations of data, and program codes executable on the processor 210. Furthermore, the memory 220 may store the program codes that operate the processor 210 to generate training data.

The memory 220 may store basic data, point cloud data, a final image, etc., and may store information about feature points generated by the feature point generation model. Furthermore, the memory may store the depth information and pose information inferred by the processor 210 through the artificial neural network model. The memory 220 may also store artificial neural network models trained by the processor 210 and the training data of each of the models.

The network unit 230 according to an embodiment of the present disclosure may be understood as a constituent unit that transmits and receives data through any type of known wired/wireless communication system. For example, the network unit 230 may perform data transmission and reception using a wired/wireless communication system such as a local area network (LAN), a wideband code division multiple access (WCDMA) network, a long term evolution (LTE) network, the wireless broadband Internet (WiBro), a 5th generation mobile communication (5G) network, a ultra wide-band wireless communication network, a ZigBee network, a radio frequency (RF) communication network, a wireless LAN, a wireless fidelity network, a near field communication (NFC) network, or a Bluetooth network. Since the above-described communication systems are only examples, the wired/wireless communication system for the data transmission and reception of the network unit 230 may be applied in various manners other than the above-described examples.

The network unit 230 may receive data required for the processor 210 to perform computation through wired or wireless communication with any system, any client, or the like. Furthermore, the network unit 230 may transmit the data, generated through the computation of the processor 210, through wired or wireless communication with any system, any client, or the like. For example, the network unit 230 may receive basic data including a captured image through communication with a picture archiving and communication system (PACS), a cloud server that performs tasks such as the standardization of medical data, the endoscope device 100, or the like. The network unit 230 may transmit various types of data, generated through the computation of the processor 210, through communication with the above-described system, server, endoscope device 100, or like.

The data to be processed by the processor 210 may be stored in the memory 220 or received through the network unit 230, and the data generated by the processor 210 may be stored in the memory 220 or transmitted to the outside through the network unit 230.

Meanwhile, although the endoscope device 100 and the computing device 200 are described as being separated in FIG. 1, this is an example, and the computing device 200 may be provided inside the endoscope device 100 and constitute a part of the endoscope device 100.

According to the present disclosure, the computing device 200 may reconstruct a body part, captured by the endoscope, in 3D based on the data obtained in various situations, so that the quality of reconstruction can be improved while being less restricted by the type of data acquired and the situation in which data is obtained.

In addition, reconstructing is performed with feature points for information about the surface of the inside of the body added, so that the accuracy of reconstruction can be increased. A blind spot region is identified based on the information about the surface, so that convenience can be provided to a medical professional who needs to determine the accuracy of an endoscopic procedure and a blind spot region on his or her own.

Figure 2:
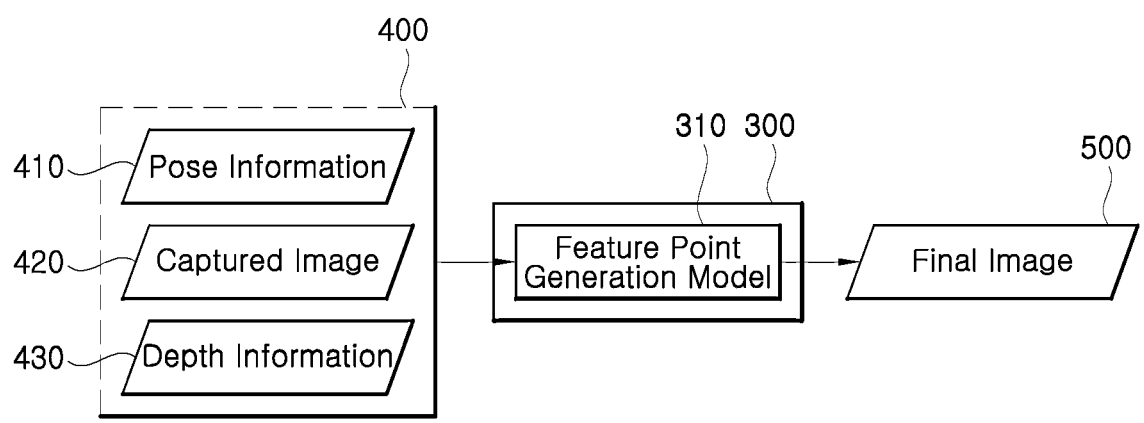
FIG. 2 is a diagram showing the configuration of a computing device according to one embodiment of the present disclosure.
Figure 3:
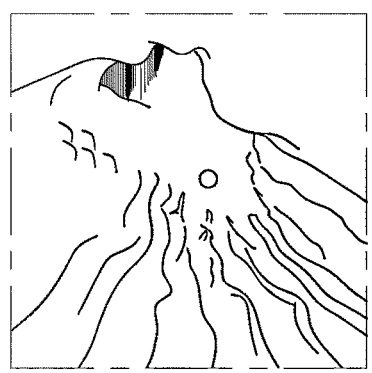
FIG. 3 is a diagram showing an example of an image generated by a feature point generation model according to one embodiment of the present disclosure.
Figure 3:
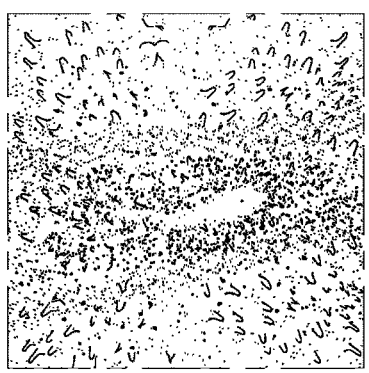
Figure 3:
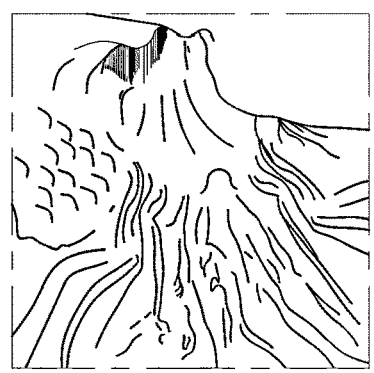
Figure 4:
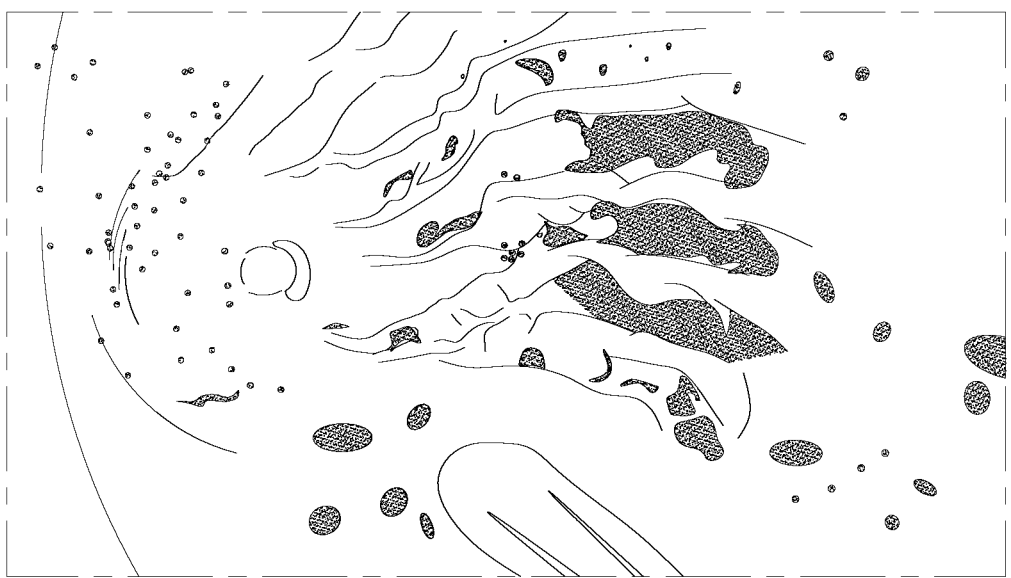
FIG. 4 is a diagram showing an example of generating feature points according to one embodiment of the present disclosure.
Figure 5:
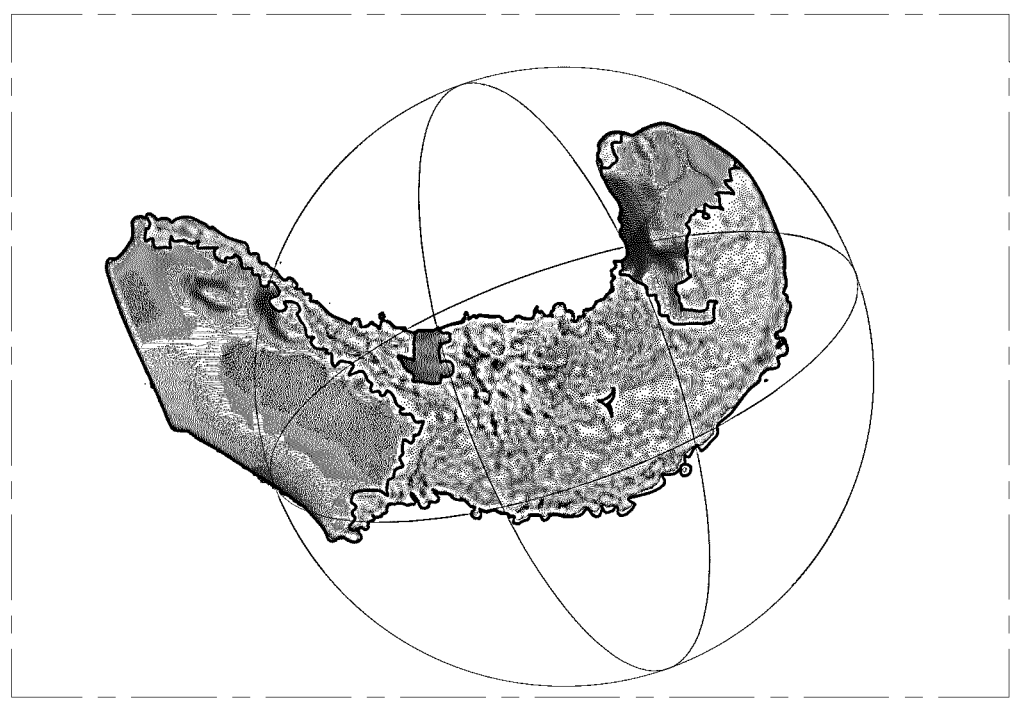
FIG. 5 is a diagram showing an example of a final image according to one embodiment of the present disclosure.

FIG. 2 is a diagram showing the configuration of a computing device according to one embodiment of the present disclosure, FIG. 3 is a diagram showing an example of an image generated by a feature point generation model according to one embodiment of the present disclosure, FIG. 4 is a diagram showing an example of generating feature points according to one embodiment of the present disclosure, and FIG. 5 is a diagram showing an example of a final image according to one embodiment of the present disclosure.

Referring to FIG. 2, the computing device 300 may generate the 3D final image 500 by using the basic data 400 obtained via an endoscope device.

The basic data 400 may include at least one of the following: pose information 410 regarding the pose of the end of the endoscopic scope, a captured image 420 of the inside of the body, and depth information 430 regarding the distance from the end of the scope to the surface of the inside of the body. For example, the pose information 410 may include coordinates and rotation values indicating a position in a 3D space. The captured image 420 may be captured by a camera provided in the endoscopic scope, or may be obtained in a virtual environment. The captured image 420 may be a two-dimensional (2D) RGB image, and may be a still image captured at a specific point in time or a moving image continuously captured.

In this case, the endoscope device may refer to a real endoscope device or an endoscope device implemented in a virtual environment. In the case of a real endoscope device, the scope of the endoscope device may be inserted into a real body or a model body, the pose information 410 may be obtained through a pose sensor provided at the end of the scope, and the captured image 420 may be obtained through a camera. Meanwhile, when a depth sensor is provided at the end of the scope, depth information up to the surface of the inside of the body may be obtained. In the case of a virtual endoscope device, the pose information 410, the captured image 420, and the depth information 430 may be obtained for the inside of a virtual body implemented in a virtual environment.

The computing device 300 may generate 3D point cloud data using the basic data 400. The point cloud data may include points corresponding to a body region captured by the endoscope device. In this case, a region captured by the endoscope device may have a higher point density, and a region corresponding to a region not captured by the endoscope device, i.e., a blind spot region, may have a lower point density.

The computing device 300 may generate the final image 500 by reconstructing the point cloud data. The final image 500 may include the 3D surface of the inside of the body. In this case, the computing device 300 may add feature points to the basic data 400 using the feature point generation model 310 to generate the final image 500. The feature points may represent the surface information of the inside of the body. More specifically, the feature points may include patterns or textures formed on the surface of the inside of the body. For example, when the body region is the large intestine, the feature points may include blood vessels, irregularities, wrinkles formed on the inner wall of the large intestine, lesions such as polyps, and the like observed on the surface of the large intestine.

Referring to FIG. 3, the feature point generation model 310 may generate an image including feature points, such as the image shown in FIG. 3(c), by adding feature points, such as the feature points shown in FIG. 3(b), to the basic data 400 with insufficient feature points, such as the data shown in FIG. 3(a).

The feature point generation model 310 may be trained through supervised learning that uses pairs of an image with a small number of feature points and an image with a large number of feature points as training data, unsupervised learning that does not require training data, or semi-supervised learning that performs training using training data including some labeled data. For example, the feature point generation model 310 may be trained through a generative artificial intelligence model. In particular, considering that it is difficult to secure a large amount of training data for endoscopic images, that labeled data needs to be generated based on clinical results, and that the frequency of training data corresponding to abnormalities is significantly low, the feature point generation model 310 may be implemented through generative artificial intelligence in the present disclosure. For example, the feature point generation model 310 may include a generative adversarial network (GAN) or a cycleGAN.

The feature point generation model 310 may add elements, including fine shapes and colors observed on the surface of the inside of the body, to an image representing the smooth inside of the body. For example, there may be added feature points representing a lesion formed on the mucosa of the stomach or large intestine, wrinkles formed on the inner wall of the stomach or large intestine, blood vessels reflected on the mucosa, curvatures formed according to the curved shape of the organ, irregularities, irregularities attributable to a lesion, a polyp, and/or the like. The feature point generation model 310 may be trained using data having similar colors and similar shapes but using data having a large number of feature points and data having a small number of feature points.

For example, the feature point generation model 310 generates images having a large number of feature points using two generators, and determines whether images having a large number of feature points are authentic using two discriminators. The generators generate images intended to deceive the discriminators, and the discriminators determine whether the generated images are authentic. By repeating this process, the feature point generation model 310 may generate images having a large number of feature points using images having a small number of feature points.

Meanwhile, the feature point generation model 310 may generate feature points based on an experimental image captured after pigment has been applied to a real body or model body.

Referring to FIG. 4, the experimental image may refer to an image obtained by capturing the shape of the distribution of pigment after the pigment has been applied to the inside of the body to emphasize the irregularities of the mucosal surface of the inside of the body. The reason for this is that the degree of staining varies depending on whether the mucosa is raised or sunken, the condition of the mucosa, and whether a lesion is included. The feature point generation model 310 may generate feature points using the shape of the distribution of the pigment from an experimental image and add them to the basic data 400.

The feature point generation model 310 may generate feature points by using the above-described methods in combination. For example, the feature point generation model 310 may generate feature points using an adversarial generative neural network, and may adjust the distribution of the feature points according to the shape in which a drug is applied.

Meanwhile, the basic data 400 may already have sufficient feature points. For example, in the case of a large intestine image, image feature points are included due to the curved shape of the large intestine, the bright and dark portions caused by the shape, the liquid collected in curves, and/or the like. In contrast, in the case of a stomach image, feature points are considerably few compared to a large intestine image due to the smooth surface of the stomach, the shape of the blood vessels, etc.

In this case, the feature point generation model 310 may generate feature points according to the above-described method by using the basic data 400 for the stomach. Furthermore, the feature point generation model 310 may extract feature points already included in the basic data 400 by using the basic data 400 for the large intestine. In other words, the feature point generation model 310 may generate feature points that are not present or insufficient in the basic data 400 by using the basic data 400, or may generate feature points present in basic data by extracting feature points from the basic data 400 that is abundant in feature points. Alternatively, reconstruction may be performed using the basic data 400 that is abundant in feature points itself.

Referring to FIG. 5, the computing device 300 may generate point cloud data using the feature points generated through the basic data 400 and the feature point generation model 310. In order to generate point cloud data, the captured image and the pose information 410 or depth information 430 included in the basic data 400 may be matched. In this case, according to the present disclosure, the accuracy of matching may be increased by adding feature points. For example, in the case of a captured image having a smooth surface or little color change, the accuracy of matching between the captured image and the pose information 410 or depth information 430 may be low because there are few feature points that serve as the basis for matching. Accordingly, according to the present disclosure, the number of reference points is increased by adding feature points to the captured image, so that the accuracy of point cloud data can be increased. The accuracy of the point cloud data may refer to the degree of similarity between the 3D final image 500, generated during reconstruction, and a data obtainment environment.

The computing device 300 may generate the 3D final image 500 of the inside of the body by reconstructing the point cloud data. In this case, the computing device 300 may generate modified point cloud data by removing points, present in a region out of a preset reference range, from the point cloud data. The computing device 300 may generate the final image 500 by reconstructing the modified point cloud data.

Meanwhile, the computing device 300 may distinguish between a portion where a surface is reconstructed smoothly and a portion where a surface is reconstructed roughly in the final image 500. The computing device 300 may determine a portion where a surface is reconstructed smoothly to be a blind spot region. When a portion in question is a portion that has not been captured by an endoscopic scope, basic data 400 corresponding to the portion may be less, and feature points added to the basic data 400 may also be fewer. Accordingly, the number of points corresponding to the corresponding portion may be small in the point cloud data, so that it may be reconstructed as a plane. In this case, the degree of roughness and smoothness may be determined based on a preset standard, and may be set based on the degree of height difference on a reference area.

Figure 6:
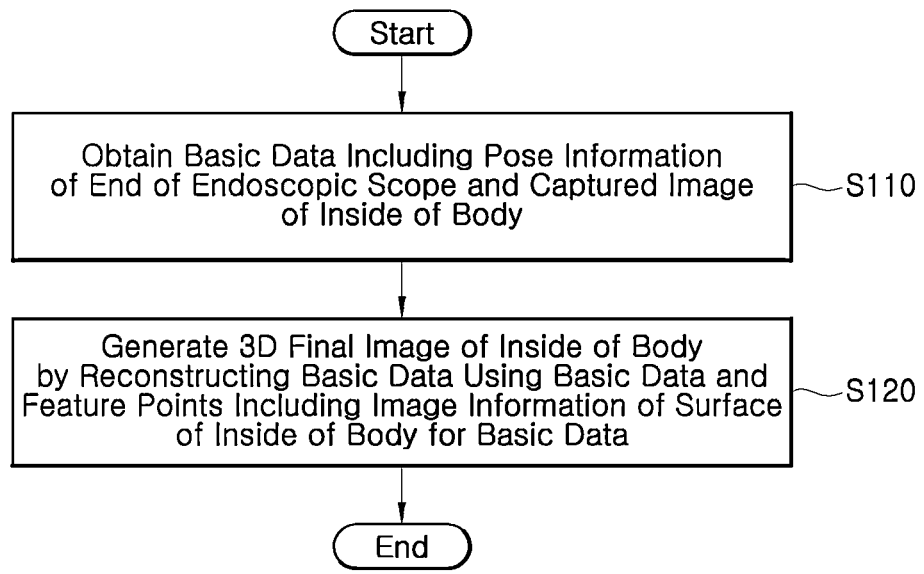
FIG. 6 is a flowchart showing a method of reconstructing an image of the inside of a body according to one embodiment of the present disclosure.

FIG. 6 is a flowchart showing a method of reconstructing an image of the inside of a body according to one embodiment of the present disclosure.

Referring to FIG. 6, the computing device 300 may obtain basic data including pose information of the end of the endoscopic scope and a captured image of the inside of the body in step S110. The basic data may further include depth information from the end of the endoscopic scope to the surface of the inside of the body. The inside of the body may be the inside of a real body, a model body, or a virtual body, but is not limited to a single specific form.

The computing device 300 may generate a 3D final image of the inside of the body by reconstructing the basic data using the basic data and the feature points including the image information of the surface of the inside of the body for the basic data in step S120. In this case, the feature points may refer to feature points included in the basic data itself, feature points extracted from the basic data, or feature points generated by the feature point generation model. The feature point generation model may generate feature points by representing patterns or textures formed on the surface of the inside of the body. In this case, the patterns or textures may include at least one of blood vessels, irregularities, wrinkles, and lesions.

Alternatively, the feature point generation model may generate feature points representing patterns or textures formed on the surface of the inside of a real body or model body by using an experimental image that is captured after a drug has been applied to the inside of the real body or model body.

The computing device 300 may generate point cloud data using the basic data and the feature points, and may generate a final image by reconstructing the point cloud data.

The computing device 300 may generate modified point cloud data by removing points, present in a region out of a preset reference range, from the point cloud data. In other words, the modified point cloud may be one in which outlier points have been removed. The computing device 300 may generate a final image by reconstructing the modified point cloud data.

Thereafter, the computing device 300 may determine the portion of the final image where a surface is smoothly reconstructed to be a blind spot region. The blind spot region may include the portion of the body that is not captured through an endoscope device.

Figure 7:
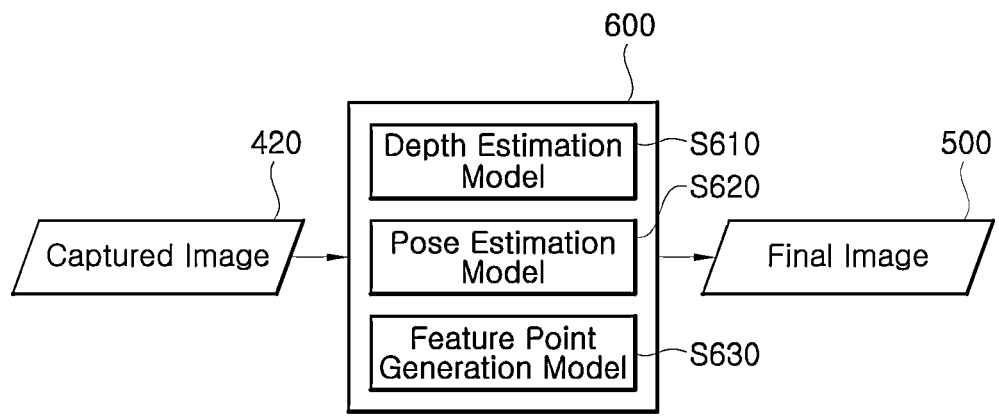
FIG. 7 is a diagram showing the configuration of a computing device according to one embodiment of the present disclosure.

FIG. 7 is a diagram showing the configuration of a computing device according to one embodiment of the present disclosure.

The computing device 600 of FIG. 7 may be similar to the computing device 300 of FIG. 2 described above, and thus, a redundant description thereof will be omitted below.

Referring to FIG. 7, the computing device 600 may generate a 3D final image using basic data including a captured image 420 of the inside of the body. The captured image 420 may be captured by a camera provided in an endoscopic scope, or may be obtained in a virtual environment.

Unlike the computing device 300 of FIG. 2, the computing device 600 of FIG. 7 may infer and obtain depth information and pose information from the captured image 420. To this end, the computing device 600 may use a depth estimation model 610 and a pose estimation model 620.

The depth estimation model 610 may infer depth information from the end of the endoscopic scope to the surface of the inside of the body based on the captured image 420 of the inside of the body. In this case, the endoscopic scope may be directly inserted into a real body or model body, or may be operated in a virtual environment.

The depth estimation model 610 may be trained using the captured image 420, which is matched with the depth information as first training data. The depth estimation model 610 may include a generative artificial intelligence model, specifically a paired image-to-image translation (Pix2Pix) model, but is not limited thereto.

The pose estimation model 620 may infer the 6D pose information of the end of the endoscopic scope inserted into the body based on the captured image 420 of the inside of the body. The pose estimation model 620 may be trained with second training data including an image, including feature points for the surface information of the inside of the body, and corresponding pose information.

Meanwhile, in the inference process of the pose estimation model 620, a captured image 420 having a large number of feature points may be input, but a captured image 420 having a small number of feature points may also be input. For example, a drug may be applied to the inside of the body, and a captured image may be input. In this case, the drug is distributed according to the curvature and irregularities of the surface of the inside of the body, there may be a large number of feature points.

When the captured image 420 having a small number of feature points is input, the feature point generation model 630 may add feature points to the captured image 420 to increase the accuracy of pose estimation. The feature point generation model 630 may add feature points through a generative artificial intelligence model as described above in conjunction with FIG. 2. Alternatively, the feature point generation model 630 may add feature points to represent the shape in which s applied. Alternatively, the computing device 600 may use a captured image 420 abundant in feature points itself or extract feature points from a captured image 420, as described above.

Figure 8:
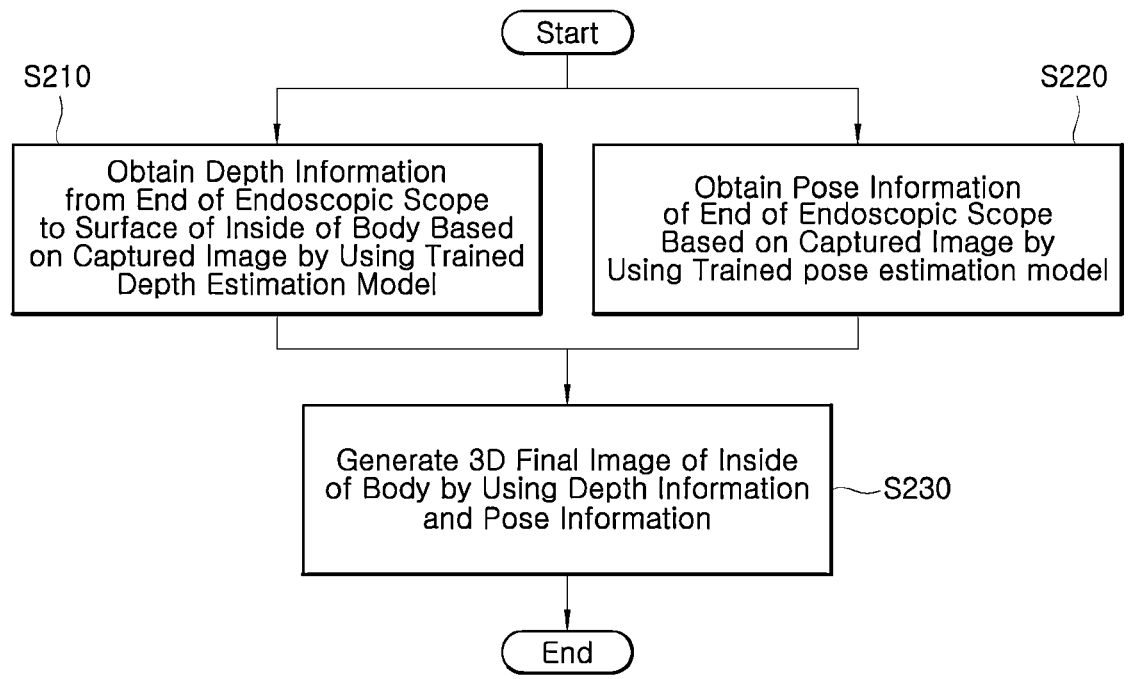
FIG. 8 is a flowchart showing a method of reconstructing an image of the inside of the body according to one embodiment of the present disclosure.

FIG. 8 is a flowchart showing a method of reconstructing an image of the inside of the body according to one embodiment of the present disclosure.

Referring to FIG. 8, the computing device 600 may obtain depth information from the end of an endoscopic scope to the surface of the inside of the body based on a captured image of the inside of the body by using a trained depth estimation model in step S210. The depth estimation model may be trained with first training data including a first training image of the inside of the body and a depth image corresponding to the first training image.

The computing device 600 may obtain the pose information of the end of the endoscopic scope based on the captured image by using a trained pose estimation model in step S220. The pose estimation model may be trained with second training data including a second training image, including feature points for the surface information of the inside of the body, and pose information corresponding to the second training image.

In this case, the computing device 600 may generate a corrected captured image by using the feature points, generated using a feature point generation model trained to represent patterns or textures formed on the surface of the inside of the body, and the captured image. The feature point generation model may be a model trained to represent patterns or textures formed on the surface of the inside of the body by using experimental images captured after drugs have been applied to the inside of the body. Alternatively, as described above in conjunction with FIG. 3, the feature generation model may be a model trained to generate patterns or textures formed on the surface of the inside of the body by using a generative adversarial neural network.

The computing device 600 may obtain the pose information of the end of the endoscopic scope based on the modified captured image by using the trained pose estimation model.

The computing device 600 may generate a 3D final image of the inside of the body by using the depth information and the pose information in step S230.

Thereafter, the computing device 600 may determine the portion of the final image where a surface is smoothly reconstructed to be a blind spot region.

The description of the present disclosure described above is intended for illustrative purposes, and those of ordinary skill in the art to which the present disclosure pertains can appreciate that the present disclosure may be easily modified forms without changing the technical into other specific spirit or essential features of the present disclosure. Therefore, it should be understood that the embodiments described above are illustrative and not restrictive in all respects. For example, each component described as being in a single form may be implemented in a distributed form. In the same manner, components described as being in a distributed form may be implemented in a combined form.

The scope of the present disclosure is defined by the following claims rather than the above detailed description, and all changes or modifications derived from the meanings and scope of the claims and their equivalent concepts should be interpreted as being encompassed within the scope of the present disclosure.

What is claimed is:

1. A method of reconstructing images of an inside of a body, the method being performed by a computing device including at least one processor, the method comprising:

obtaining basic data including pose information of an end of an endoscopic scope, a captured image of an inside of a body, and depth information from the end of the endoscopic scope to a surface of the inside of the body; and generating point cloud data using the basic data and feature points including image information of the surface of the inside of the body for the basic data, and generating a three-dimensional (3D) final image of the inside of the body by reconstructing the point cloud data, wherein the depth information is obtained based on the captured image of the inside of the body by using a trained depth estimation model.

2. The method of claim 1, wherein the feature points are generated by a feature point generation model that is trained to represent patterns or textures formed on the surface of the inside of the body.

3. The method of claim 2, wherein the patterns or textures include at least one of blood vessels, irregularities, wrinkles, and lesions.

4. The method of claim 2, wherein the feature point generation model generates the feature points by representing a shape in which a drug is applied to the surface of the inside of the body.

5. The method of claim 1, wherein generating the 3D final image comprises:

generating modified point cloud data by removing points, present in a region out of a preset reference range, from the point cloud data; and generating the final image by reconstructing the modified point cloud data.

6. The method of claim 1, further comprising determining a portion of the final image, in which a surface is smoothly reconstructed, to be a blind spot region;

wherein the blind spot region includes a portion of the inside of the body that is not captured through the endoscopic scope.

7. A method of reconstructing images of an inside of a body, the method being performed by a computing device including at least one processor, the method comprising:

obtaining depth information from an end of an endoscopic scope to a surface of an inside of a body based on a captured image of the inside of the body by using a trained depth estimation model;

generating a modified captured image by using feature points generated using feature point generation model and the captured image, and obtaining pose information of the end of the endoscopic scope based on the modified captured image by using a trained pose estimation model; and generating a three-dimensional (3D) final image of the inside of the body by using the depth information and the pose information.

8. The method of claim 7, wherein the depth estimation model is trained with first training data including a first training image of the inside of the body and a depth image corresponding to the first training image.

9. The method of claim 7, wherein the pose estimation model is trained with second training data including a second training image including feature points for surface information of the inside of the body and pose information corresponding to the second training image.

10. The method of claim 9, wherein the feature point generation model trained to represent patterns or textures formed on the surface of the inside of the body.

11. The method of claim 10, wherein the feature point generation model generates the feature points by representing a shape in which a drug is applied to the surface of the inside of the body.

12. A computing device for reconstructing images of an inside of a body, the computing device comprising:

memory configured to store basic data including pose information of an end of an endoscopic scope, a captured image of an inside of a body, and depth information from the end of the endoscopic scope to a surface of the inside of the body; and a processor configured to generate point cloud data using the basic data and feature points including image information of the surface of the inside of the body for the basic data, and a three-dimensional (3D) final image of the inside of the body by reconstructing the point cloud data, wherein the depth information is obtained based on the captured image of the inside of the body by using a trained depth estimation model.

13. A computing device for reconstructing images of an inside of a body, the computing device comprising:

memory configured to store a captured image of an inside of a body; and a processor configured to obtain depth information from an end of an endoscopic scope to a surface of the inside of the body based on the captured image by using a trained depth estimation model, generate a modified captured image by using the captured image and feature points generated using feature point generation model, obtain pose information of the end of the endoscopic scope based on the modified captured image by using a trained pose estimation model, and generate a three-dimensional (3D) final image of the inside of the body by using the depth information and the pose information.

* * * * *